United States Patent [19]

Figuera

[11] Patent Number: 5,169,378
[45] Date of Patent: Dec. 8, 1992

[54] INTRA-VENTRICULAR EXPANSIBLE ASSIST PUMP

[76] Inventor: Diego Figuera, Av. Concha Espina 61, 28016 Madrid, Spain

[21] Appl. No.: 558,898

[22] Filed: Jul. 26, 1990

[51] Int. Cl.$^5$ ............................................. A61N 1/362
[52] U.S. Cl. .......................................... 600/16; 623/3
[58] Field of Search ........................ 623/3; 600/16, 18

[56] References Cited

U.S. PATENT DOCUMENTS

| | | | |
|---|---|---|---|
| 3,568,659 | 3/1971 | Karnegis | 600/18 |
| 4,195,623 | 4/1980 | Zeff et al. | 600/18 |
| 4,245,622 | 1/1981 | Hutchins, IV | 600/18 |
| 4,588,404 | 5/1986 | Lapeyre | 623/3 |

Primary Examiner—Randy C. Shay
Attorney, Agent, or Firm—Ladas & Parry

[57] ABSTRACT

An expansible assist pump for implantation through the femoral artery (left ventricle) or the femoral vein (right ventricle) is used as circulatory support in patents with severe cardiac shock. The pump comprises a body pump, or external chamber, having a double lumen wall, that is expansible and of variable rigidity, and a transvalvular segment, or flexible "neck" of the pump, that conforms itself to the situation or position of "open" or "closed" of the aortic or pulmonary valves and avoids the need of using a valve in the discharge of blood from the pump. An internal balloon having a progressive wall thickness is provided and causes a sequential rhythm of inflation and deflation. The pump further comprises a uni-directional nozzle system that functions as an admission valve, and a conducting catheter including two conduits, one for the pneumatic drive and activation of the balloon and the other for the injection of liquid or gas at high pressure into the double wall system of the body pump thus causing its expansion and variable rigidity.

16 Claims, 7 Drawing Sheets

INTRA-VENTRICULAR EXPANSIBLE ASSIST PUMP

FIELD AND BACKGROUND OF THE INVENTION

This invention relates to an intraventricular expansible assist pump for use as circulatory support in patients with a severe ventricular cardiac shock.

This very serious complication can be developed under the following circumstances:

(a) In patients with acute myocardial infarction in a state of cardiogenic shock. In the United States over a million and a half acute myocardial infarctions are reported every year, of which about 60,000 develop cardiogenic shock.

(b) In patients who, after an open heart operation, cannot be weaned off the extracorporeal circulation on account of myocardial failure and low cardiac output. Every year over 200,000 operations with extracorporeal circulation are carried out all over the world. Approximately in 7% of the cases (some 15,000 patients per year) it is not possible to wean the patient off the extracorporeal circulation. Half of these cases can be solved with an IABP (Intra-aortic counterpulsation) system and inotropic drugs, but the other half requires a more efficient mechanical circulation support.

(c) As a bridge to heart transplants. The scarcity of donors and the long Waiting lists make it every day more necessary to have an available system to sustain the life of the waiting recipient.

(d) Severe chronic cardiomyopathies in a situation of low cardiac output. Estimated in over 25,000 cases per year.

(e) Accidents in hemodynamic labs, especially in cases when angioplasties are done in critical cases.

Nowadays there exist several systems of mechanical circulatory assistance, some available without restrictions and others still in the clinical research stage.

The main characteristics of the most important ones are recorded hereafter for the purpose of establishing comparisons with the pump of the invention.

(i) Intra-Aortic Counterpulsation (IABP)

In the case of left ventricular failure, IABP reduces the overload and increases the coronary flow, but in the case of severe heart failure it cannot maintain an adequate circulation (it supplies only 0.8 l/min/m$^2$). It has the advantage of a quick and easy implantation and, furthermore, the possibility of being percutaneously implanted, but in patients with cardiogenic shock, it has been shown that it does not reduce mortality. (See Bregman et al.: A pulsating assist device (PAD) for improved protection during cardiopulmonary bypass. Ann Thorac Surg 24:547, 1977)

(ii) Femoro-Femoral By Pass with Magnetic Centrifugal Pumps

This can be carried out using the percutaneous technique of Phillips (Phillips S. J.: Percutaneous Cardiopulmonary bypass and innovations in clinical counterpulsation. Crit Care Clin 2:297,1986) or by the femoral cutdown technique. This system also allows a rapid implantation but its efficiency is limited. It can maintain a reasonable circulatory support for 24 to 48 hours, during which time more definitive measures should be accomplished. It can be very useful in hemodynamic laboratories, and in intensive care units. Its major problem is that it does not unload the left ventricle or, if it does, in an ineffective way. For this reason, it can only be used for a very short period of time.

(iii) Ventricular Assistance with Centrifugal Pumps, Roller Pumps and Thoracotomy If the state of cardiogenic shock persists, in spite of the IABP and of inotropic drugs, it is necessary to have recourse to a more efficient system. This can be the left ventricular assistance system (LVAS) or the right ventricular assistance system (RVAS) or assistance of both ventricles (BVAS) by means of magnetic or roller pumps but after performing a thoracotomy. With such systems of circulatory assistance plus, if necessary, a membrane oxygenator (ECMO), it is possible to maintain a patient with cardiogenic shock in a reasonable thermodynamic situation for six to ten days, but after that time many problems arise.

(iv) Heterotopic Artificial Ventricle (VAD)

There are several models of artificial ventricles that can be placed in the external part of the thorax and that can cover totally or partially the function of the assisted ventricle. The most common models are the following: Symbion AVAD; Pierce-Donachy Thoratec; Novacor LVAS and Thermedic LVAS. The former two are pneumatically driven. The Novacor, electrically driven, can be implanted.

With the above systems, a mono or bi-ventricular assistance can be performed. Their efficiency in supporting circulation is greater than the previous methods and the duration of the assistance can be lengthened to two or three months. They have the disadvantage of requiring a thoracotomy and that the cannula implantation can be cumbersome. This proceeding involves a complicated and risky operation and, for this reason, the indication is in many cases delayed for too long. This results in further deterioration of the patient's condition and worse results.

(v) Total Artificial Hearts (TAH)

This extreme system of circulatory assistance has been developed during the last twenty years. There are several devices, some still in the experimental stage. The most commonly used have been Symbion, Jarvick-7 (161 implantations as of April 1990). Liotta, Akutsu and Phoenix have been used for one patient each. The Berlin and Ellipsoidof Unger have been used in four cases, and that of Pennsylvania State University, in two. The most usual indication for a total artificial heart (TAH) has been as a "bridge" for heart transplantation in case of irreversible acute cardiac failure. It has the advantage that the "bridge situation" can be maintained for a long time which makes long delays possible in the case of difficult recipients with antigenic problems. Its main inconvenience is produced by the irreversibility of having the patient's heart removed, and the technical difficulties of the implantation which are greater than in the case of a heart transplantation.

We have reached the conclusion that the ideal circulatory assistance system must fulfill the following conditions:

1) Easy to implant (without thoracotomy) through peripheric arteries or veins.

2) Capacity to unload the assisted ventricle and to take on 60% to 80% of its normal function.

3) Location of the system inside the ventricle to avoid the losses of energy involved in intercalated cannulae.

4) The non-necessity of mechanical or biological valves.

5) The possibility of maintaining the device for periods of two or three months or even permanently, and of renovating it.

6) The ability to work without being synchronized with the assisted ventricle.

7) The device should offer the possibility of being used as a permanent assistance in chronic cases.

SUMMARY OF THE INVENTION

The intra-ventricular assist pump of the invention is similar in duration and efficiency to the artificial ventricles (VAD), and the mechanical heart (TAH), but it presents the great advantage that its implantation is without thoracotomy and that such implantation is as easy as that of the balloon counterpulsation (IABP) or femoro-femoral bypass. It may be driven by a pneumatic drive unit.

DETAILED DESCRIPTION OF THE INVENTION

For a better understanding of the pump of the invention, reference is made to FIGS. 1-7b of the drawings.

Figures 1, 2A, 2C, 2F:
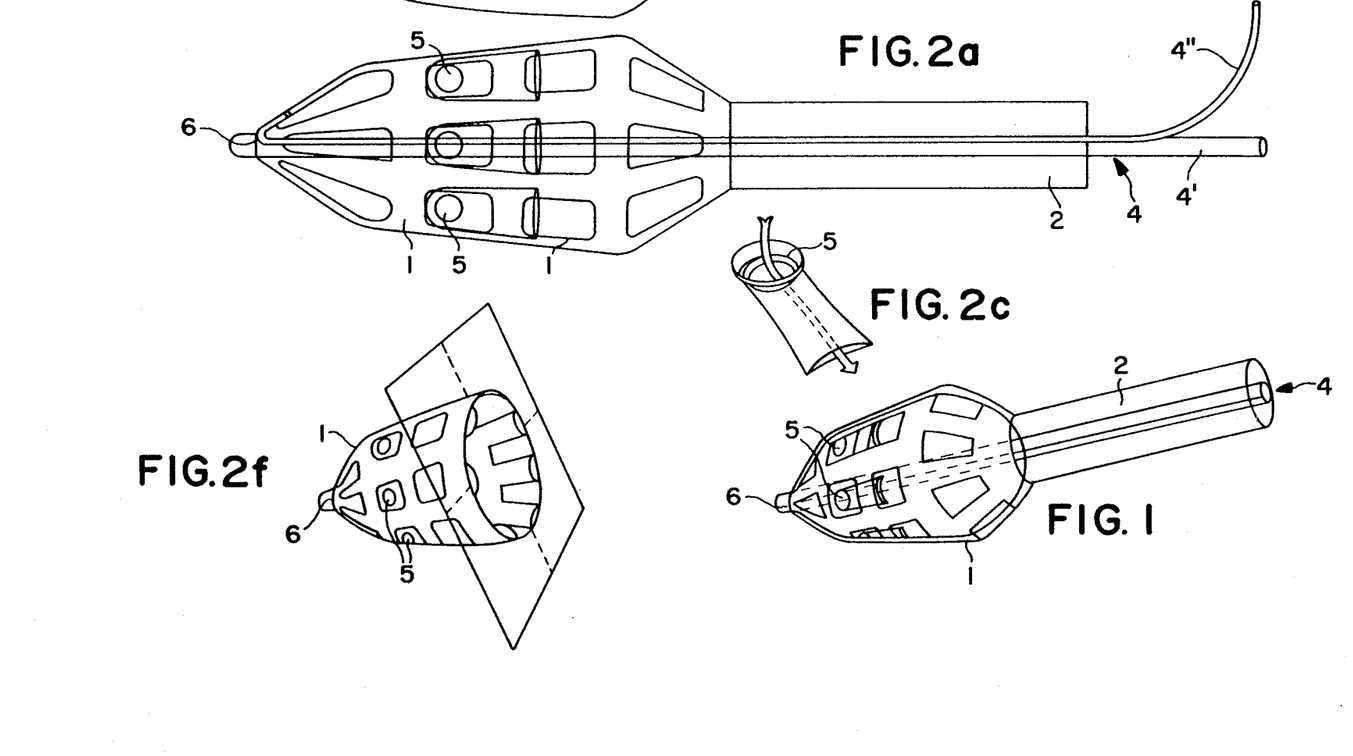
FIG. 1 is a perspective view of an intraventricular assist pump according to the invention.
FIGS. 2a to 2f show various components of the intraventricular assist pump of the invention, as shown in FIG. 1.
Figure 2B:
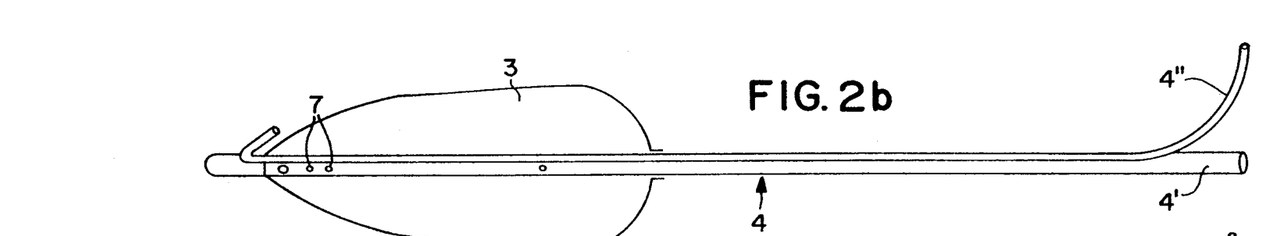
Figure 2D:
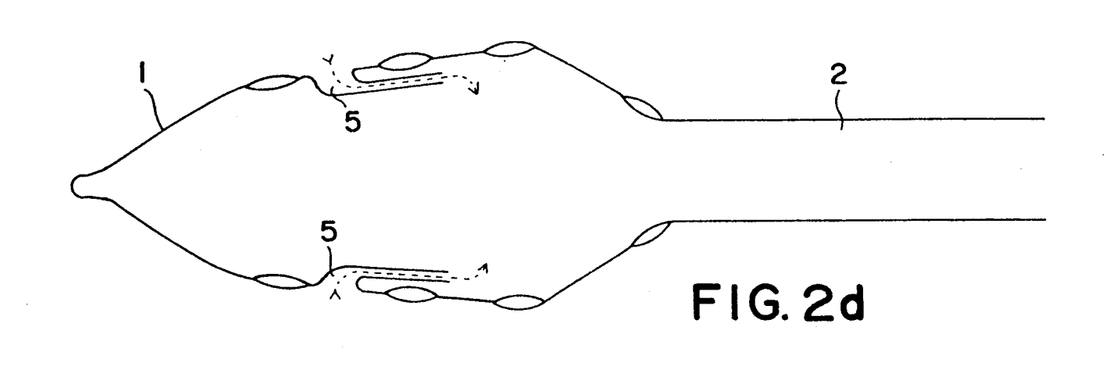
Figure 2E:
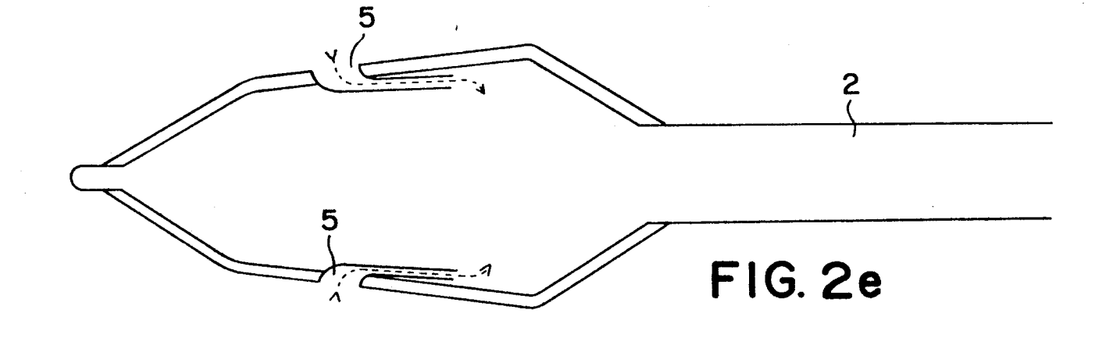

With reference to FIG. 1, there is shown a perspective view of the pump. In FIGS. 2a to 2f, the different components of the pump are shown. FIG. 2a illustrates the pump body 1 and the transvalvular segment 2. In FIG. 2b, there is shown an internal balloon 3 with a two-way conducting catheter 4. The nozzle system 5 is illustrated in FIG. 2c, while FIGS. 2d and 2e show longitudinal sections of the pump body 1. In FIG. 2f, there is shown a transverse section of the pump body 1.

In FIG. 2a to 2f, the different parts of the pump are shown. With reference to FIGS. 2a, 2d and 2e, there is shown the body pump, or external chambers which is an irregular ovoid whose main feature is that it is "expansible" on account of its "double wall system", as represented in the Figures, because, included in the wall, there is a tubular net connected with a two way catheter (4) at point 6. When there is no liquid, or gas, in the thickness of the wall, this body pump 1 or external chamber is flexible, pliable, and able to be wrapped (although it is not elastic). Nevertheless, it can be expanded and converted into a "rigid chamber" by means of the injection of pressurized liquid or gas into the double wall system that becomes engorged. This system is represented in FIG. 2a by a tubular net, but the rigidity can also be obtained by means of other double wall system, like interconnected cells, sponge tissue sandwich and so on.

A transvalvular segment 2, "neck", or distal part of the pump comprises a tube of some 16 mm diameter, is constructed of plastic bio-compatible material, as that of the body pump, but with very thin walls, which implies that it can easily collapse. It is through this that the blood, contained in the body pump, exits when the internal balloon 3 is distended.

When the pump is located in the left ventricle 8, the "neck" runs through the aortic valve and adapts itself to its situation of being "open" or "closed", without interfering in the function. When in the right ventricle 8', the position is the same through the infundibulum and the pulmonary valve. The manner in which this tube is constructed avoids the need for using a valve in discharge of blood from the pump.

The internal balloon 3, as shown in FIG. 2d, is also constructed with a bio-compatible material and has a pyriform shape. Its main characteristic is that the thickness of its wall increases from the narrower distal part to the wider proximal part. The reason for such a difference is to provoke an inflation, somewhat sequential, progressive, from the pointed end on, thus making the ejection of the blood contained in the body pump easier.

Reference is now made to the nozzle system, shown in FIGS. 2c, 2d and 2e. The shaded section of FIG. 2a represents the "nozzles" 5 that can be seen in detail in FIG. 2c. These nozzles establish the communication between the internal part of the ventricle and the internal part of the body 1 of the pump or external chamber, allowing the entrance of the blood in its interior when the internal balloon 3 collapses and when a vacuum is applied. The valves are of the unidirectional type (from the ventricular cavity to the cavity of the body pump), because the distal end is closed when at rest and only opens when the interior balloon 3 deflates. The airtightness of the closure increases when the pressure of the internal part of the body pump 1 increases due to the inflation of the balloon.

The two way conducting catheter shown in FIG. 2b has two conduits 4' and 4". A larger diameter conduit 4' is meant for the inflation and deflation of the internal balloon 3 by means of air or gas at high pressure that is supplied by the external drive unit. At the distal end, it includes holes 7 for the passage of the gas.

The lesser diameter conduit 4" serves for the introduction of the liquid or the inert gas at high pressure for the purpose of expanding the external chamber or the body pump 1. It is connected at point 6 with the double wall system of the chamber.

The double wall of the chamber is represented by a tubular system, but it can be constructed in many different ways, for example, little intercommunicated cells; spongy texture; two walls interdependent through internal connections, etc. But the main idea of this external chamber is that, by means of an injection into its double wall system, whether with liquid or gas at high pressure, it expands and becomes a rigid structure. The chamber is of varying rigidity, not distendible, so that, on one hand, it avoids collapse when a vacuum is produced in the internal balloon and, on the other hand, protects the myocardium from the internal pressure provoked by the inflation of the balloon.

Operation of the Pump

This pump, with some variations in its structure, can be used for assistance to the left as well as to the right ventricle.

Left ventricle pump

For the purpose of this description, it will be assumed that the pump is being used to assist the left ventricle.

Figure 3:
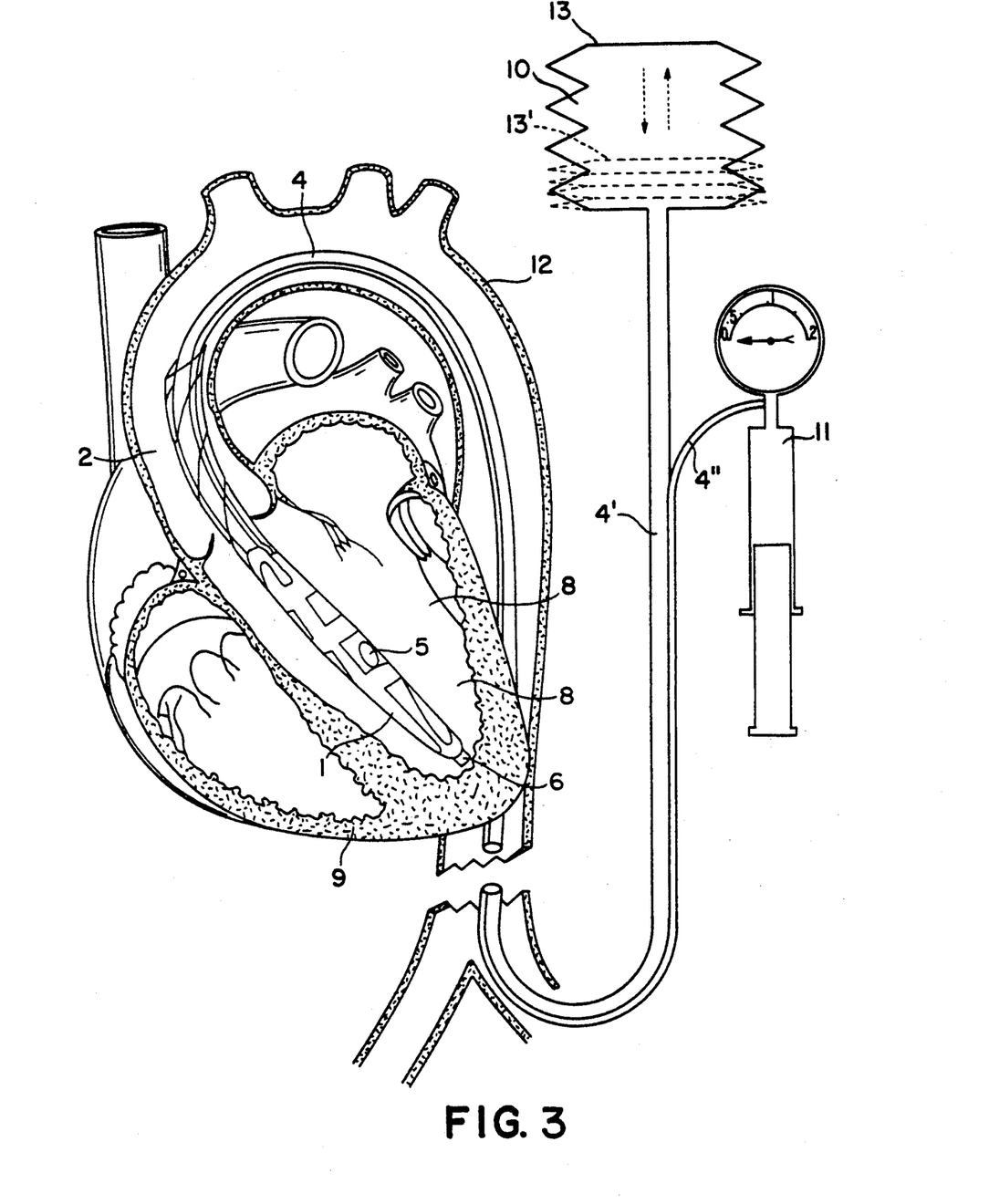
FIGS. 3, 6, 7a, and 7b show the intraventricular assist pump of FIGS. 1 and 2, in the heart, in operation.

1. Initial position (FIG. 3)

The pump 1 is wrapped to its two way conducting catheter 4, with the internal balloon 3 deflated and the transvalvular segment 2 also wrapped to the catheter. The compressor 10 of the drive unit is in the position of rest and the pressure of the circuit of expansibility at 0. Under the above described conditions, the pump 1 has been introduced into the left ventricle through the femoral artery 12, keeping the whole "pump-catheter" in this position by a very thin sheath of plastic material that is not represented in the drawings.

Figure 4:
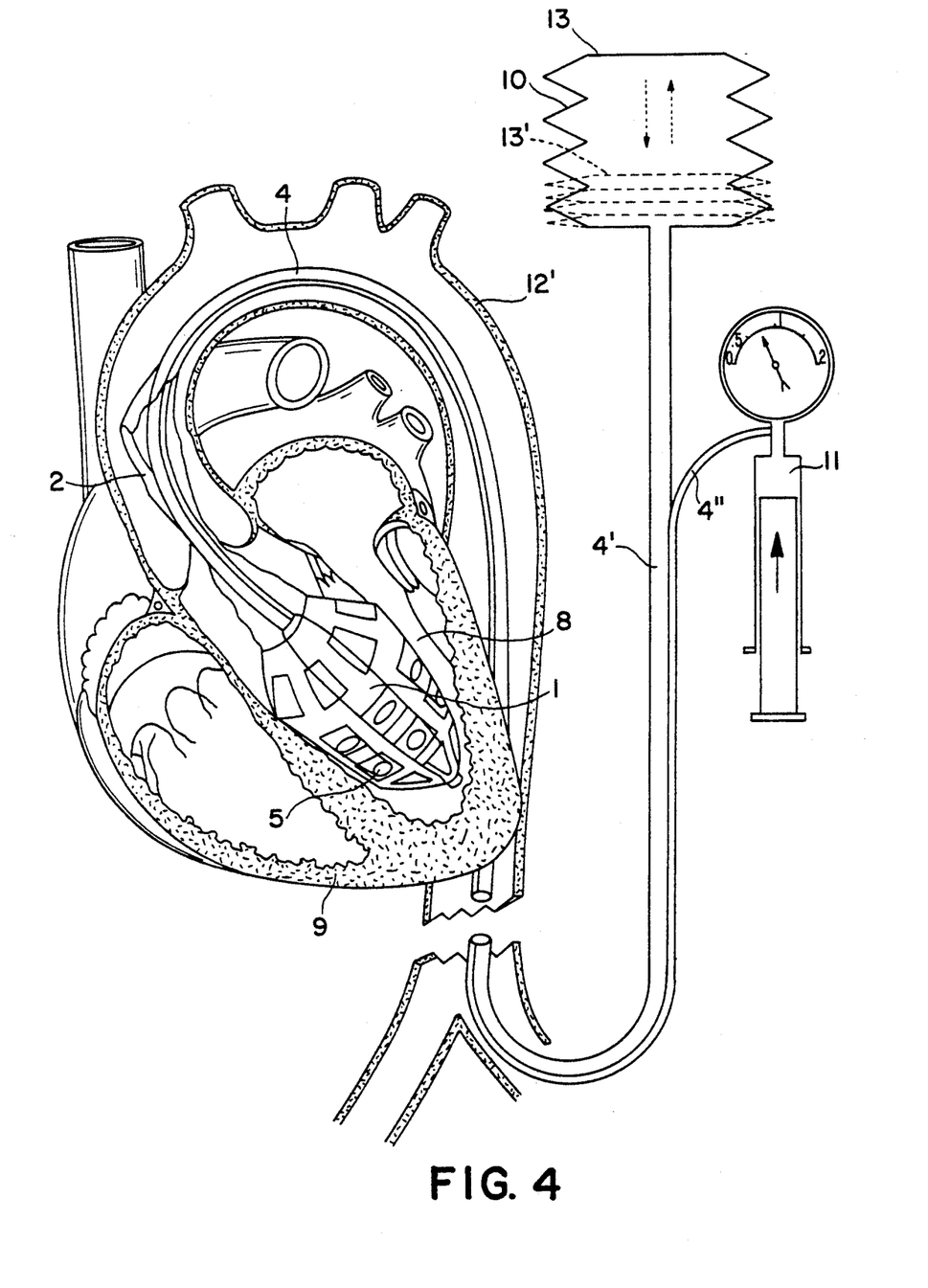

2. Position. Body pump expanded (FIG. 4)

In order to expand the body pump 1, the liquid or gas has to be introduced into the double wall circuit by means of the pump 11 until it reaches an adequate pressure calculated to be between $\frac{1}{2}$ and 1 atmosphere. This pressure depends on the pressure that ventricle to be assisted can reach. In every hemodynamic situation, the pressure must be the minimum necessary so that the external chamber remains expanded durinq the cardiac cycle and does not collapse.

During the process of expansion, the nozzles 5 remain open and the body of the pump fills with blood. If in this moment one ventricular systole should take place, there will be no problem, only that the passing of the blood from the ventricular cavity to the chamber will increase and the blood will be expelled from the chamber and from the ventricle through the pump neck and through the aortic valve.

Figure 5:
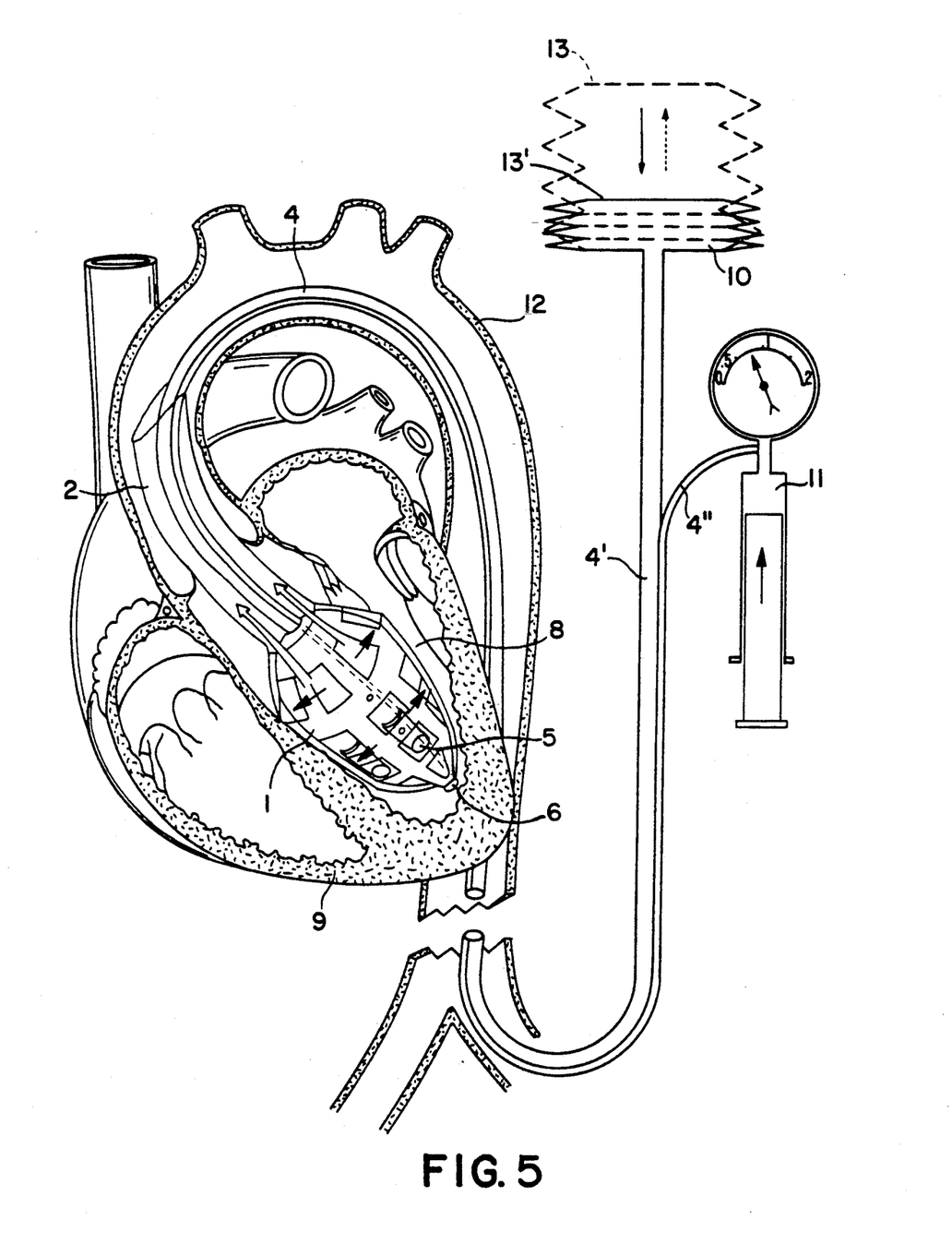

3. Functioning of the pump: Systole (FIG. 5)

When the drive unit 10 is put into action and the rest position 13 of the compressor moves to that of pressure 13', the inflation of the internal balloon 3 takes place, the nozzles 5 close and the blood contained in the chamber, or body 1 of the pump, is ejected through the aorta without the pressure exerted by the internal balloon interfering or rebounding on the ventricular wall. What we could call the "systole" of the assistance pump has taken place.

Figure 6:
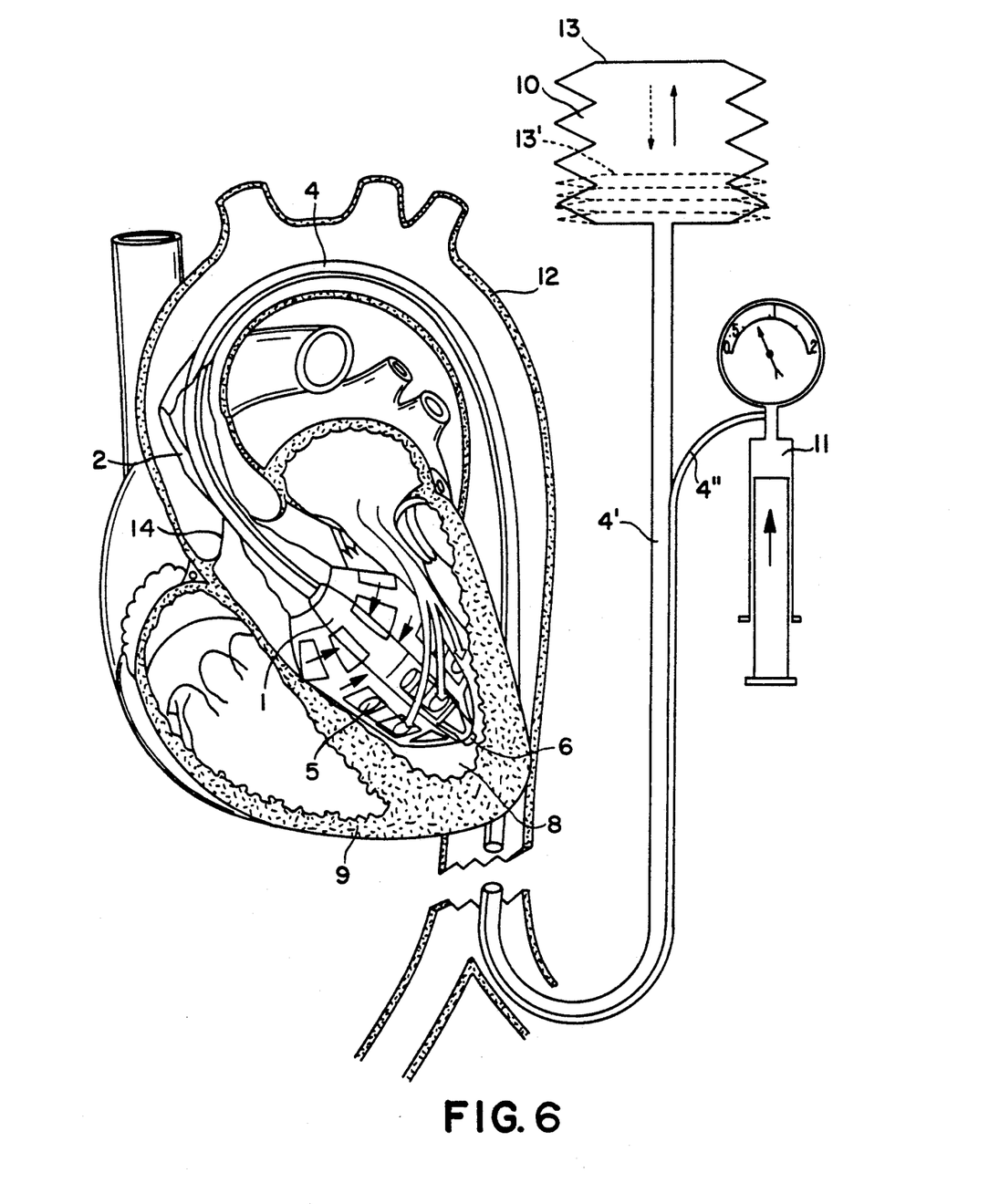

4. Functioning the pump. Diastole (FIG. 6)

When the drive unit applies the vacuum into the system and the position of pressure 13' passes to vacuum 13, the internal balloon deflates and collapses, creating a vacuum situation inside the body of the pump. At this moment, the blood contained in the ventricle 8 and that which comes from the left auricle through the mitral valve penetrates into the interior of the chamber 1 through the nozzles 5. The depression produced in the ventricle and in the interior of the chamber closes the aortic valve 14 and collapses the transvalvular segment 2. Valve 14 and segment 2 close, adapting themselves to the conducting catheter 4.

This action explains why the neck or transvalvular segment 2 of the pump has a very thin wall. When it has no pressure inside it may collapse and adapt or conform itself to the situation or position of the aortic valve 14, without interfering in the function thereof or doing so in a minimal way.

5. End of the cycle

When the preceding phase ends, the cycle of the pump comes to an end. This cycle can be synchronized with the ventricle by means of the synchronizer of the drive unit, but the synchronization is not indispensable, as there is very little hemodynamic repercussion even if the ventricular systole interferes with the pump "diastole", or the "systole" of the pump with the ventricular diastole.

Right Ventricle Pump

In order to assist the right ventricle, the same kind of pump can be used, but with certain modifications of form and procedure. See FIGS. 7a and 7b.

Figure 7A:
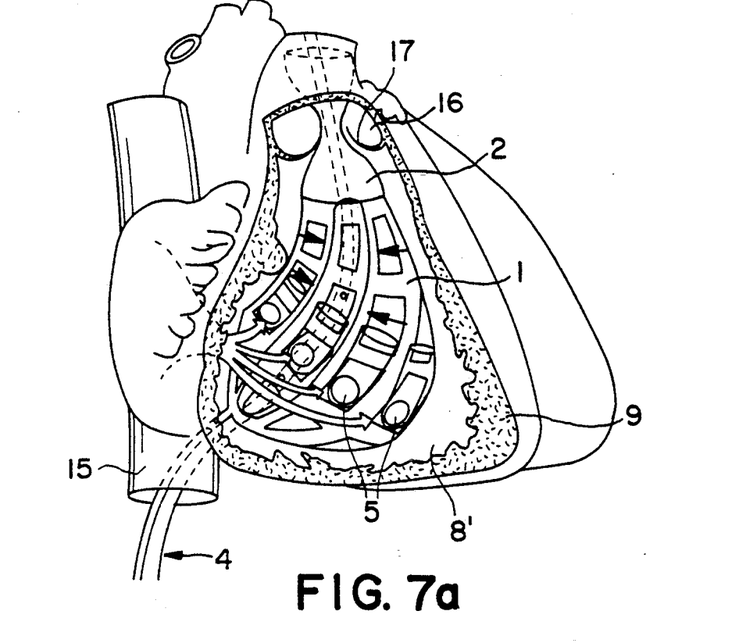
Figure 7B:
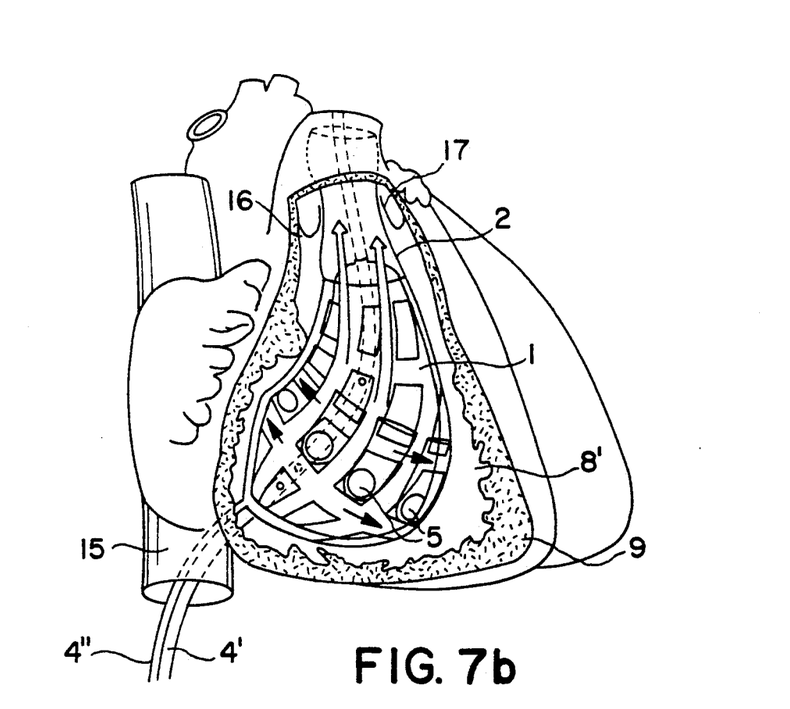

1) the right ventricular cavity 8' is through femoral vein and the inferior vena cava 15, or through the jugular vein and superior vena cava.

2) The position of the body 1 of the pump is inverted, so that the neck or transvalvular segment 2 is in the distal part of the external chamber and it passes through the infundibulum 16 of the right ventricle 8' and the pulmonary valve 17. The connection with the circuit of the double wall of the external chamber or body 1 of the pump is achieved in the proximal part of the body, closest to the tricuspid valve.

3) The two way catheter 4 soon loses the small diameter conduit 4'', namely, the one that carries the liquid or gas at high pressure with the object of expanding the external chamber, as the connection with the double lumen system takes place in the more proximal part. This catheter ends in a sharp segment that runs along the inside of the neck 2 of the pump which assists in its introduction through the infundibulum 16 and the pulmonary valve 17, for which it has to have the adequate preformed shape.

4) The shapes of the body pump 1 and of the internal balloon 3 are non-symmetric and have a curved shape to conform to the shape of the right ventricle 8' and infundibulum 16. The phases of diastole (FIG. 7a) of the pump and of the systole (FIG. 7b) take place in the same way as described above for the left ventricle 8.

As the pressure inside the double lumen of the wall of the body pump can be regulated, and its rigidity varied, it is possible to adapt that rigidity to the pressure existing inside the cavity of the assisted ventricle. If the pressure exerted by the ventricle rises unexpectedly in one heart beat, a situation of "occupied ventricle" will not result because the body pump yields, contracting with the ventricle, with little interference with the ventricular unload. For this reason the pressure inside the wall of the body chamber must be regulated at the minimum necessary to maintain it expanded during all the cardiac cycle "normal" in the hemodynamic situation of the patient.

As mentioned above, the synchronization of the pump with the heart beat is not indispensable, though the drive unit 10 must be provided with such possibility as well as with all the elements that are necessary to maintain and control all its functions: inflation and deflation; high and low pressures; vacuum; expansibility pressures; ventricular flow; EKG, and so on. It must also have all the security measures common in these kinds of drive units.

As the need for assistance decreases on account of the recuperation of the ventricle, it is possible to slowly reduce the pressure in the expansibility circuit as well as the amount of the inflation of the balloon 3, until the final removal of the pump is effected. This may be done as follows:

1. The pressure of the expansibility circuit is totally suppressed and vacuum is applied to facilitate the total emptiness. To ease the emptiness the action of the internal balloon 3 can be maintained for a few seconds.

2. The internal balloon 3 is collapsed and left inactive.

3. The body pump is withdrawn by pulling at the catheter, while at the same time it is rotated to facilitate the wrapping.

4. The femoral vein or artery is reconstructed.

I claim:

1. An intraventricular expansible assist pump comprising:

a double walled pump body which is expansible and of variable rigidity, the body defining a chamber;

a hollow neck portion extending from one end of the pump body, the neck portion being in communication with the chamber;

an internal balloon located in the chamber;

at least one nozzle means associated with the pump body for permitting flow of liquid unidirectionally from outside the pump body into the chamber thereof;

a conducting catheter member extending from the pump body exterior to the pump body interior having a first conduit communicating with the interior of the external balloon for controlling inflation and deflation of the internal balloon, and a second conduit connected to a space defined between the two walls of the double wall of the pump body for injection of fluid into said space to selectively expand the pump body and vary the rigidity thereof.

2. A pump as claimed in claim 1 wherein the pump body comprises at least one aperture in the pump wall one of said at least one nozzle means being located in a respective aperture to permit the flow of fluid from outside the pump body into the chamber thereof.

3. A pump as claimed in claim 2 wherein the conducting catheter member extends from a source, through the neck portion, the first conduit extending from the neck portion to communicate with the internal balloon, the second conduit extending from the neck portion to communicate with the space defined within the double wall.

4. A pump as claimed in claim 1 wherein the internal balloon has a wall of thickness which progressively decreases from an end of the balloon near the neck portion to the other end thereof.

5. A pump as claimed in claim 1 wherein the first conduit has one end thereof for connection to a source of pneumatic power, the other end thereof being connected to the internal balloon to selectively inflate and deflate the internal balloon.

6. A pump as claimed in claim 1 wherein the second conduit has one end thereof for connection to a source of fluid for injection into the space, the other end thereof being connected to the pump body so as to convey the fluid to the space defined by the double wall.

7. A pump as claimed in claim 1 wherein the neck portion comprises a flexible thin-walled material to facilitate its operation during both open and closed cycles in aortic or pulmonary valve.

8. A pump as claimed in claim 1 wherein the pump body is of an irregular void shape, the double wall comprising an integrated tubular system and defining the pump body and a plurality of apertures in the pump body wall, one of said at least one nozzle means being located in each aperture.

9. A pump as claimed in claim 1 wherein the pump body is flexible and pliable when no or little fluid is contained in the space defined within the double wall and a substantially rigid body when the space within the double wall is injected with fluid under pressure.

10. A pump as claimed in claim 1 wherein the neck portion comprises a tube of substantially 16 mm in diameter, the tube being comprised of bio-compatible material, the walls of the tubes being sufficiently thin to permit easy collapse thereof.

11. A pump as claimed in claim 1 wherein each nozzle includes a uni-directional valve whereby fluid flows only from outside of the pump body into the chamber thereof.

12. A pump as claimed in claim 1 wherein the first conduit of the conducting catheter member has a diameter for conveyance of air or gas under pressure into the balloon, the first conduit having one end for connection to a gas source, the other end being received within the interior of the balloon, the first conduit having apertures at the end thereof within the balloon to permit gas to pass between the interior of the balloon and the first conduit, the second conduit of the conducting catheter member having a diameter smaller than the first conduit for conveyance of liquid or inert gas at high pressure, the second conduit having one end for connection to an external source and the other end being connected to the space defined within the double wall of the pump body.

13. A process for pumping blood in a heart, the process comprising:

providing a pump having: a double walled pump body which is expansible and of variable rigidity, the body defining a chamber; a hollow neck portion extending from one end of the pump body, the neck portion being in communication with the chamber; an internal balloon located in the chamber; at least one nozzle means associated with the pump body for permitting flow of liquid unidirectionally from outside the pump body into the chamber thereof; a conducting catheter member extending from the pump body exterior to the pump body interior and having a first conduit communicating with the interior of the internal balloon for controlling inflation and deflation of the internal balloon, and a second conduit connected to a space defined between the two walls of the double wall of the pump body for injection of fluid into said space to selectively expand the pump body and vary the rigidity thereof;

implanting the pump body in a location where assistance in blood pumping is required;

injecting liquid into the space defined within the double wall of the pump body through the second conduit of the conducting catheter member so as to provide the pump body with the desired rigidity;

inflating the internal balloon whereby blood in the chamber of the pump body will be forced therefrom through he neck portion, blood being incapable of passing outwardly from the chamber to outside of the pump body through the nozzle means; and deflating the internal balloon thereby creating a vacuum within the chamber whereby blood from outside the chamber flows therein through the nozzle means.

14. A process as claimed in claim 13 wherein the implanting step comprising implanting the pump into a left ventricle of a heart through the femoral artery.

15. A process as claimed in claim 13 wherein the implanting step comprises implanting the pump into a right ventricle of a heart through the femoral or jugular vein.

16. A process as claimed in claim 13 further comprising the step of varying the pressure of the fluid within the two walls of the double wall to facilitate adaptation of the pump body to different hemodynamic situations.

* * * * *